(12) United States Patent
Chiang (10) Patent No.: US 8,857,266 B2
(45) Date of Patent: Oct. 14, 2014

(54) TENSOMETER FOR SIMULTANEOUSLY EVALUATING POLYMERIZATION STRESSES, SHRINKAGE AND MODULUS DEVELOPMENT

(75) Inventor: Martin Chiang, Olney, MD (US)

(73) Assignee: The United States of America, as Represented by the Secretary of Commerce, The National Institute of Standards and Technology, Gaithersburg, MD (US)

( * ) Notice: Subject to any disclaimer, the term of this patent is extended or adjusted under 35 U.S.C. 154(b) by 315 days.

(21) Appl. No.: 13/282,600

(22) Filed: Oct. 27, 2011

(65) Prior Publication Data

US 2012/0085178 A1 Apr. 12, 2012

(51) Int. Cl.
*G01N 3/08* (2006.01)
*G01N 3/20* (2006.01)

(52) U.S. Cl.
CPC .......... *G01N 3/20* (2013.01); *G01N 2203/0092* (2013.01)
USPC .............................................. 73/826; 73/849

(58) Field of Classification Search
USPC .................................... 73/826, 847, 849, 855
See application file for complete search history.

(56) References Cited

U.S. PATENT DOCUMENTS

| | | | | |
|---|---|---|---|---|
| 4,369,653 A | * | 1/1983 | Ciosek, Jr. .................. | 73/150 R |
| 4,562,743 A | * | 1/1986 | Bonine ........................... | 73/828 |
| 5,519,211 A | * | 5/1996 | Bur et al. .................. | 250/227.19 |
| 6,050,138 A | * | 4/2000 | Lynch et al. ................. | 73/150 A |
| 6,871,550 B2 | * | 3/2005 | Eichmiller ....................... | 73/827 |
| 7,240,545 B1 | * | 7/2007 | Jennings ......................... | 73/149 |

OTHER PUBLICATIONS

Watts, D.C.; Marouf, A.S.; Al-Hindi, A.M.; "Photo-polymerization shrinkage-stress kinetics in resin-composites: methods development"; Dental Materials 19 (2003) 1-11.

Stolov, Andrei A.; Xie, Tao; Penelle, Jacques; Hsu, Shaw L.; "Simultaneous Measurement of Polymerization Kinetics and Stress Development in Radiation-Cured Coatings: A New Experimental Approach and Relationship between the Degree of Conversion and Stress"; Macromolecules 2000, 33, 6970-6976.

* cited by examiner

*Primary Examiner* — Max Noori
(74) *Attorney, Agent, or Firm* — Mark E. Bandy; Rankin, Hill & Clark LLP (57) ABSTRACT

The present invention relates to apparatus and method for evaluating the development of PS during polymerization of dental restorative composites, which includes using a tensometer for measuring deflection of a calibrated cantilever beam induced by PS and calculating PS from the measured deflection. A tensometer according to an embodiment of the present invention can be used to quantify PS at varying beam locations and heights, and determine trend in PS development as a function of beam length. More importantly, in the present invention, the development of polymerization shrinkage and the elastic modulus can be simultaneously obtained in real time.

6 Claims, 10 Drawing Sheets

TENSOMETER FOR SIMULTANEOUSLY EVALUATING POLYMERIZATION STRESSES, SHRINKAGE AND MODULUS DEVELOPMENT

STATEMENT OF FEDERAL RIGHTS

This work was funded in part by the National Institute of Standards and Technology under the Department of Commerce.

FIELD OF THE INVENTION

The present invention generally relates to measurement of stress during curing of a polymer material and, more particularly, is concerned with evaluating the development of polymerization shrinkage and modulus during curing of a polymer material.

BACKGROUND OF THE INVENTION

Human tooth structures (mineral and proteinaceous components) are adversely affected by caries, and the resulting cavities usually do not fully regenerate. In such scenarios, the affected tooth frequently requires reconstruction using adhesive and restorative dental materials. Polymeric dental composites have been widely used in the restoration of tooth decay or cavity that occurs by primary caries or traumatic events. These materials, along with appropriate adhesives, are noted for their efficacy in restoring the function and appearance of tooth structure. However, these dental restorations may fail due to secondary caries, and replacement of failed restorations creates extra pain, anxiety, and economic burdens for the patients. Dental restorations fail for a variety of reasons. For example, magnified stresses (stress singularity) at or near the tooth/composite interface due to the mismatch of tooth and restorative mechanical properties are important contributors to failure. Polymerization shrinkage that occurs during dental composite curing process has been implicated as a major stress source for the interfacial stress singularity. This shrinkage can lead to marginal micro cracks and subsequent micro leakage at or near the composite-tooth interface, which permits bacteria to pass beneath the restoration surface and ultimately cause secondary (recurrent) caries.

Polymerization stresses (PS) of resin-based dental materials have been measured using a variety of methods. In general, the development of PS is measured through perturbing physically constrained specimens, and the resulting PS can be determined from responses of constraints to the perturbation. A cantilever-beam based instrument has been used for determining PS from the constrained polymerization shrinkage. Composite (or resin) specimens are mechanically attached to a cantilever beam via a quartz rod adhesively in contact with the specimen, and the specimen is also adhesively attached to a fixed lower rod. Upon polymerization, the composite shrinkage stress induces a deflection in a calibrated cantilever beam, and the beam deflection is measured using a linear variable differential transformer (LVDT). The PS is calculated from the measured deflection using a mathematical relationship. Such instruments have not been found to be sensitive to subtle differences in PS. For example, beam deflection measured by existing system does not reflect exclusively the specimen deformation due to shrinkage, but includes deformation from the shrinkage-transmitting rods in the system. In the existing system, calculations for deducing polymerization stress do not take into account geometrical conditions of beam. Further, calibration of the existing system needs compressed air and a load cell (extra instrumental setups) and unnecessary experimental procedures, which become a burden for periodic recalibration of the system. Furthermore, the existing system is solely used for the measurement of polymerization stress development, which cannot be functionally related to the extent of polymerization shrinkage or the modulus development.

Consequently, a need exists for a cantilever-based instrument for measuring the development of PS, shrinkage, and modulus with enhanced sensitivity to specimen shrinkage and beam geometry.

SUMMARY OF THE INVENTION

The present invention provides an apparatus and method for evaluating the development of PS during polymerization of dental restorative composites. A tensometer according to an embodiment of the present invention can be used to quantify PS at varying beam locations and heights, and determine trend in PS development as a function of beam length. (inventive subject matter which overcomes the problems and satisfies the needs previously considered. Then, all of the advantages and attainments of the present invention are briefly explained.)

Beam deflection measured by a tensometer according to an embodiment of the present invention reflects exclusively the specimen deformation due to shrinkage, and does not include deformation from the shrinkage-transmitting rods in the system. A tensometer according to an embodiment of the present invention takes into account geometrical conditions of beam. Further, periodic calibration of a tensometer according to an embodiment of the present invention can be performed without undue burden.

Accordingly, the present invention relates to system for evaluating the development of PS during polymerization of dental restorative composites, which includes a cantilever beam having a predetermined aspect ratio and a predetermined spring constant mounted on a beam mount; a slider coupled to the cantilever beam, wherein the slider is capable of moving on a guiding groove along the length of the cantilever beam; a first collet coupled to the slider; a second collet coupled to a base; a first connector rod attached to the first collet and a second connector rod attached to the second collet, wherein the first and second connector rods have a predetermined spring constant, wherein the ratio of the spring constant of the first and second connector rods to the spring constant of the cantilever beam is greater than a predetermined value; a beam position measuring device coupled to the cantilever beam, wherein the beam position measuring device is coupled to the cantilever beam at distal end; and a processor for determining shrinkage of a polymer at the predetermined time intervals.

More specifically, the base comprises a slot along the length of the base and the polymer shrinkage tensometer further includes: a support beam coupled to the base, wherein the support beam is perpendicular to the base; and a beam mount coupled to the support beam, wherein the beam mount is located at the distal end of the support beam. In one aspect of the present invention, the second collet is capable of being positioned on the slot along the length of the base.

One embodiment of the present invention further includes a sample holder coupled to the first and second connector rods, wherein the longitudinal axes of the first and second connector rods and the sample holder is substantially aligned, wherein the sample holder is capable of receiving polymer material, wherein the sample holder is capable of holding the polymer material during a curing process. Another embodiment of the present invention further includes a light source to facilitate a curing process of the polymer in the sample holder. More specifically, the light from the light source is directed to the polymer in the sample holder through an axial cavity in the first collet and the first connector rod, wherein the first rod is substantially transparent to allow the light from the light source to reach the polymer.

In one aspect of the present invention, the beam position measuring device measures a deflection of the cantilever beam member at predetermined time intervals. In another aspect of the present invention, the processor determines linear shrinkage and elastic modulus of the polymer at the predetermined time intervals.

The present invention further relates to a method for determining the development of polymeric shrinkage during polymer material curing, which include the operative steps of: coupling a first sample of the polymeric material having a predetermined length to a cantilever beam at a first predetermined position; exposing the polymeric material to a light source, wherein the exposing to the light source enables a curing process of the polymeric material; measuring deflection of the cantilever beam at predetermined time intervals until the polymeric material curing is complete; calculating shrinkage stress of the polymeric material exposed to curing light at each of the predetermined time intervals; coupling a second sample of the polymeric material having the predetermined length to the cantilever beam at a second predetermined position; repeating the steps of exposing, measuring, and calculating for the second sample of the polymeric material attached to the cantilever beam, wherein the steps of exposing, measuring, and calculating are performed at the predetermined time intervals; and determining linear shrinkage and elastic modulus of the polymeric material at the predetermined time intervals. In one aspect of the present invention, the light source is ultraviolet light. In another aspect of the present invention, the curing of the polymeric material causes shrinkage of the polymeric material and measuring deflection of the cantilever beam at the predetermined time intervals includes detecting the shrinkage of the polymeric material In another embodiment of the present invention, the method further includes the step of storing the stress values at each of the predetermined time intervals.

One embodiment of the present invention related to a method for determining the development of polymeric shrinkage and modulus during polymer material curing, which include the operative steps of: curing a first sample of the polymeric material having a predetermined length, wherein the first sample of the polymeric material is coupled to a cantilever beam at a first predetermined position; measuring deflection of the cantilever beam at predetermined time intervals until the polymeric material curing is complete; coupling a second sample of the polymeric material having the predetermined length to the cantilever beam at a second predetermined position; curing the second sample of the polymeric material; measuring deflection of the cantilever beam at the predetermined time intervals until the second sample of the polymeric material curing is complete; and determining linear shrinkage and elastic modulus of the polymeric material at the predetermined time intervals.

In one aspect of the present invention, the method for determining the development of polymeric shrinkage and modulus during polymer material curing, further include the operative steps of: calculating shrinkage stress of the polymeric material exposed to curing light at each of the predetermined time intervals; and storing the stress values at each of the predetermined time intervals. The curing the first and second samples of the polymeric material include exposing the polymeric material to a light source. In one embodiment, the curing the first and second samples of the polymeric material enables shrinkage of the polymeric material, and measuring deflection of the cantilever beam at the predetermined time intervals comprises detecting the shrinkage of the polymeric material.

DETAILED DESCRIPTION

As used throughout the disclosure, the following terms, unless otherwise indicated, shall be understood to have the following meanings.

"Tensometer" refers to a cantilever based device used to evaluate tensile stress of a material due to a physical constraint and other tensile properties of materials, such as tensile strength.

"Collet" refers to a holding device that forms a collar around the object to be held and exerts a strong clamping force on the object when it is tightened, usually via a tapered outer collar.

"Tensile load" refers to a load induced from the constraint to the volume change of material.

"Spring constant" refers to force exerted by a spring to the distance it is stretched.

The present invention relates to apparatus and method for evaluating the development of PS during polymerization of dental restorative composites, which includes using a tensometer for measuring deflection of a calibrated cantilever beam induced by composite stress and calculating PS from the measured deflection. A tensometer according to an embodiment of the present invention can be used to quantify PS at varying beam locations and heights, and determine trend in PS development as a function of beam length.

Figure 1:
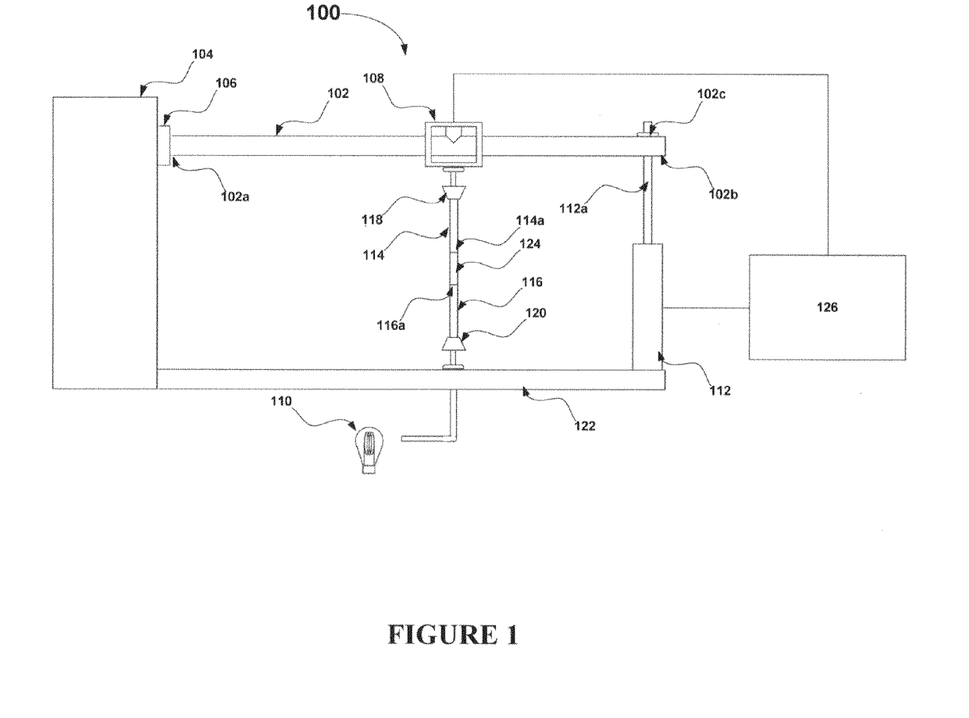
FIG. 1 is a perspective view of a tensometer in accordance with an embodiment of the present invention.

Referring now to the drawing, and more particularly, to FIG. 1, there is shown a tensometer, generally designated 100, which comprises embodiments of the present invention. Tensometer 100 includes cantilever beam 102, beam support 104, beam mount 106, slider 108, light source 110, linear variable differential transformer (LVDT) 112, upper connector rod 114, lower connector rod 116, upper collet 118, lower collet 120, base 122, composite specimen 124, and processor 126. Proximal end 102a of cantilever beam 102 is coupled to support beam 104 with beam mount 106 such that cantilever beam 102 is perpendicular to beam support 104. In one embodiment of the present invention, beam mount 106 is attached to beam support 104 with mounting screws. Cantilever beam 102 is mounted on beam mount 106 by using a clamping mechanism that, when loose, allows cantilever beam 102 to slide in and out of beam mount 106 along the longitudinal axis of the cantilever beam 102. When tight, clamping mechanism of beam mount 106 locks cantilever beam 102 at a predetermined length perpendicular to beam support 104. Clamping mechanism of beam mount 106 preferably provides for adjustment of length of cantilever beam 102 and for convenient replacement of cantilever beam 102 made from materials of differing stiffness.

Figure 2:
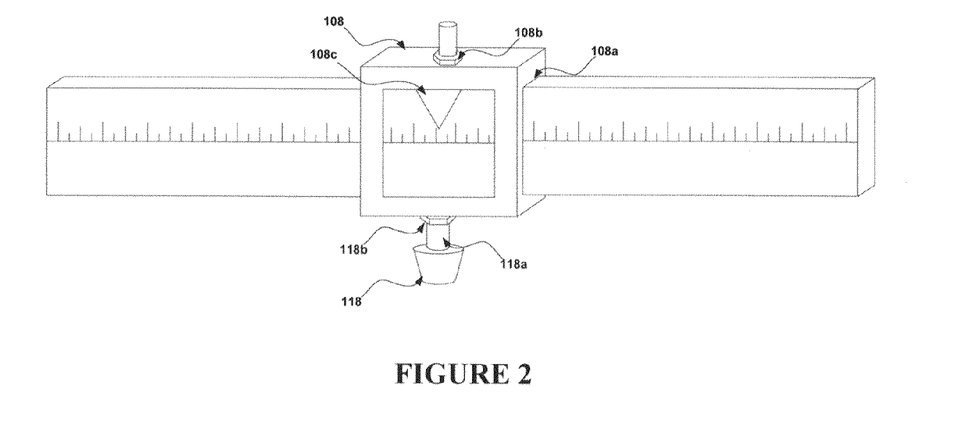
FIG. 2 is a perspective view of an exemplary tensometer slider used in an embodiment of the present invention.

Slider 108 is mounted on cantilever beam 102 and serves as a point of reference for cantilever beam 102 position measurements. FIG. 2 illustrates structural details of an exemplary slider 108 used in accordance with an embodiment of the present invention. As shown in FIG. 2, slider 108 includes a slot 108a through which cantilever beam 102 may be inserted. Slot 108a is positioned such that slider 108 is capable of sliding along cantilever beam 102 in a direction substantially parallel to the longitudinal axis of cantilever beam 102. Slider 108 includes a clamping mechanism 108b for locking slider 108 at a predetermined position on cantilever beam 102. Pointer 108c indicates position of slider 108 on cantilever beam 102 ruler 102a. Upper collet 118 is coupled to bottom of slider 108 using a threaded upper collet shaft 118a, which extends upward through slot 108b of slider 108. Upper collet mounting nut 118b is used secure upper collet shaft 118a at a desired position. Loosening upper collet mounting nut 118b allows upper collet shaft 118a to move up and down slot 108b of slider 108, and tightening upper collet mounting nut 118b locks upper collet shaft 118a at a desired position.

Figure 3:
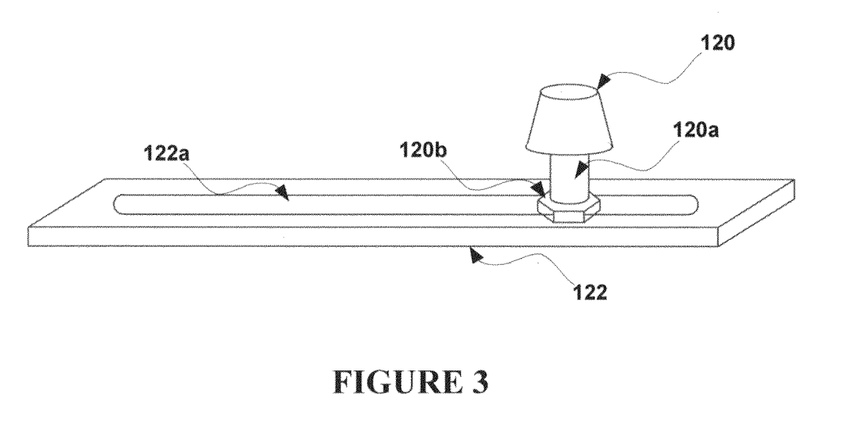
FIG. 3 shows an exemplary tensometer base used in an embodiment of the present invention.

FIG. 3 illustrates structural detail of base 122 used in accordance with an embodiment of the present invention. Referring now to FIG. 3, lower collet 120 is coupled to base 122 using a threaded lower collet shaft 120a, which extends downward through slot 122a of base 122. Slot 122a extends along the longitudinal axis of base 122 and parallel to the longitudinal axis of cantilever beam 102. Lower collet mounting nut 120b is used secure lower collet shaft 120a at a desired position. Loosening lower collet nut 120b allows upper collet shaft 120a to move along the longitudinal axis of slot 122a of base 122, and tightening lower collet nut 120b locks lower collet shaft 120a at a desired position on base 122.

Upper connector rod 114 is coupled to slider 108 using upper collet 118 and lower connector rod 116 is coupled to base 122 using lower collet 120, as shown in FIG. 1. In one embodiment of the present invention, upper connector rod 114 and lower connector rod 116 are designed to include high spring constant and capable of transmitting light through them. Exemplary connector rods include quarts, glass, and the like. Upper connector rod 114 is inserted into and secured by upper collet 118. A lower end of upper connector rod 114 protrudes downward from the upper collet 118 and has a lower end face 114a. Lower connector rod 116 is inserted into and secured by the lower collet 120. The upper end of lower connector rod 116 protrudes upward from lower collet 120 and has an upper end face 116a. Upper end face 116a of the lower connector rod 120 and lower end face 114a of lower connector rod 114 are in a generally opposed and spaced relation with a gap between them. Lower collet 120 includes a cavity along its longitudinal axis to allow light from light source 110 to flow through lower collet 120 to lower connector rod 116. Lower connector rod 116 is substantially transparent to allow light from light source 110 to flow through connector rod 116 to composite specimen 124.

During testing, composite specimen 124 generally resides in the space between upper end face 116a of the lower connector rod 120 and lower end face 114a of lower connector rod 114. In one embodiments of the present invention, a sample holder is coupled to the first and second connector rods 114-116 such that the longitudinal axes of the first and second connector rods 114-116 and the sample holder is substantially aligned. The sample holder is capable of receiving uncured composite specimen 124 and capable of holding composite specimen 124 during a curing process. Composite specimen 124 is coupled to upper end face of the lower connector rod 116 and the lower end face of the upper connector rod 114. In one embodiment of the present invention, composite specimen 124 is chemically linked to upper end face of the lower connector rod 116 and the lower end face of the upper connector rod 114. In embodiments of the present invention where connector rods 114-116 are made of quartz, composite specimen is bonded to connector rods 114-116 via a silane-coupling chemistry. In such embodiments, the faces of connector rods 114-116 are silanized to promote adhesion between composite specimen and connector rods 114-116.

LVDT 112 measures deflection of cantilever beam 102 caused by shrinkage of composite specimen 124. LVDT 112 is coupled to cantilever beam 102 and measures relative position or change in relative position of cantilever beam 102. LVDT 112 is coupled to cantilever beam 102 using an armature shaft 112a extending from top face 112b of LVDT 112 to cantilever beam 102. Armature shaft 112a is inserted into a slot located at distal end 102b of cantilever beam 102 and extending along the vertical axis of cantilever beam 102. Armature shaft 112a is secured at top of slot, at distal end 102b, using a clamping nut 112c.

In one aspect of the present invention, tensometer 100 further includes a processor 126 communicatively coupled to LVDT 112 and configured to track measurement readings from LVDT 112 over a time period during the curing of composite specimen 124. In some embodiments of the present invention, processor 126 may also be coupled to other sensors and transducers to monitor and record the onset, completion and intensity of light from light source 110, the temperature of composite specimen 124 during the curing process, or other response being measured in the sample or measurement system. Processor 126 may further process measurement information to calculate force and stress due to curing composite specimen 124 as a function of the measurement information obtained from LVDT 112. Processor 126 may calculate development of polymer stress in composite specimen 124 using the method shown in FIG. 8.

Operation of a cantilever-based tensometer 100 according to an embodiment of the present invention is generally based upon beam theory where a tensile load generated by a shrinking composite specimen pulls down a cantilevered beam. The tensile load causes the beam to bend downward and this downward bending is measured as beam deflection with a linear variable differential transformer (LVDT). The tensile load is then calculated based upon a calibration constant for the beam.

In evaluating the development of polymeric stress in a dental composite, several parameters of a tensometer sample can be varied to mimic different in vivo conditions. Beam length can be varied by moving collet position along the length of the beam. This will vary the spring constant and can establish the maximum allowed displacement for any particular sample size and material. A single surface restoration with high wall-to-wall resistance can be mimicked by a very short beam length and representing a low wall-to-wall displacement. A wide restoration with thin tooth support can be mimicked by a longer beam length with greater displacement during shrinkage. Another adjustable parameter is the sample size. Diameter of sample can be changed by varying sample connector rod diameter. Changing the connector rod diameter changes the ratio of bonded to unbounded surface areas (C-factor, the configuration factor). The second sample dimension that can be changed is the sample length. This can be adjusted by moving the end-to-end distance between the two connector rods. A shorter sample length raises the C-factor, while a longer length reduces the C-factor. The unbounded length can also be set to mimic the intercuspal width of a dental restoration. The diameter controls the area of the bonded surface (area of opposing cavity walls) while the distance between the rods changes the wall-to-wall distance (cavity width).

Curing rates and methods can be changed to mimic clinical conditions. Curing can be done either through the connector rod or by curing from the side of the sample. Any lamp can be used in any configuration for curing. Exemplary lamps include quartz tungsten halogen lamp, plasma arc lamp, laser curing light, light-emitting diode (LED) light, and the like. The instrument will mark the data when the sample is illuminated and when the lamp goes off. It will also mark as many times as the sample is illuminated. The curing time can be controlled either by the instrument, or the light can be controlled manually with the curing light controls.

Under normal operation of tensometer 100 in accordance with an embodiment of the present invention, light is transmitted from light source 110 through lower connector rod 116 onto composite specimen 124. Exemplary light sources include ultra-violet light, visible light having a wavelength of about 474 nm and an output of about 300 mW/cm$^2$, and the like. The irradiation process initiates polymerization resulting in shrinkage of composite specimen 124. As composite specimen 124 shrinks during the curing process, the shrinkage exerts force (F) between upper end face 116a of the lower connector rod 120 and lower end face 114a of lower connector rod 114. Force (F) is transmitted through upper connector rod 120 to cantilever beam member 102, causing the relative position of cantilever beam member 102 to change.

Figure 4:
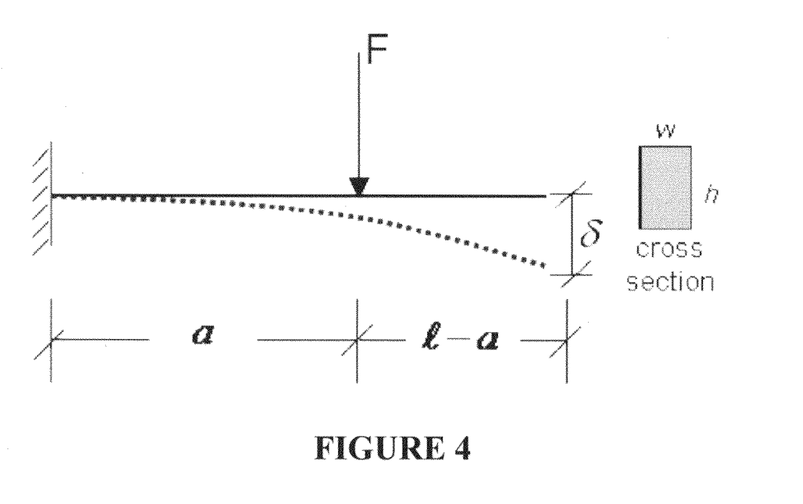
FIG. 4 illustrates a graphical schematic of cantilever beam in accordance with an embodiment of the present invention.

LVDT 112 measures this change in relative position of cantilever beam member 102, or beam deflection ($\delta$). FIG. 4 shows a graphical schematic of cantilever beam 102 configuration in accordance with an embodiment of the present invention. Processor 126 calculates force (F) using equation (1).

$$F = \frac{6\delta EI}{a^2(3l - a)} \quad (1)$$

where $\delta$ is cantilever beam deflection; l and a are the distances between the clamped edge and the LVDT and sample location, respectively; E and I ($=(wh^3)/12$) are Young's modulus and moment of inertia of beam; h and w are the height and width of beam cross-section, respectively. The polymerization stress ($\sigma$) is force (F) divided by the cross-section area of specimen (A), as shown in equation (2).

$$\sigma = \frac{F}{A} \quad (2)$$

Equation (1) is derived based on a linear elastic system and Euler-Bernoulli beam theory in which the vertical deflection of a beam is assumed to arise from bending while deflection due to shearing is negligible. Under these stated conditions, beam length (l) is much greater than beam depth (h) (large slenderness ratio, i.e., length/depth (l/h)). Effective length (a), or span, of cantilever beam 102 in the configuration shown in FIG. 4 is the length of cantilever beam 102 from beam support 104 to the position indicated by slider pointer 108d, which is the position where composite specimen 124 is coupled to cantilever beam 102 and polymerization stress is exerted. Aspect ratio of cantilever beam 102 is defined as the ratio of effective beam length (a) to beam height (h), and is equal to (a/h). In order to minimize effects of beam shearing on beam deflection, aspect ratio (a/h) of cantilever beam 102 should be greater than or equal to 8. In order to avoid in-plane stretching (diaphragm strain) of cantilever beam 102 and satisfy aforementioned requirements for the Euler-Bernoulli beam theory, deflection ($\delta_s$) of cantilever beam 102 at the position where composite specimen 124 is coupled to cantilever beam 102 should be less than half the thickness (h) of cantilever beam 102 (i.e., $\delta_s/h < 0.5$).

Figure 5:
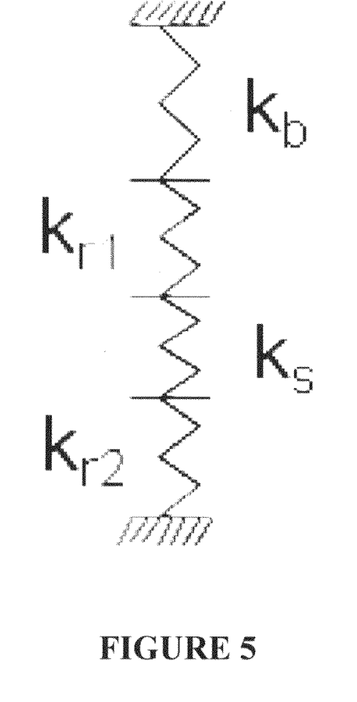
FIG. 5 illustrates a model using springs to represent tensometer in accordance with an embodiment of the present invention.

Cantilever beam 102, upper connector rod 114, lower connector rod 116 and composite specimen 124 of tensometer apparatus 100, as shown in FIG. 1, can be modeled as four springs in series. FIG. 5 illustrates a graphical schematic of tensometer apparatus 100 with four components: cantilever beam, upper connector rod, lower connector rod, and composite specimen. Spring constants for the components are: cantilever beam is $$k_b \left( = \frac{3EI}{a^3} \right);$$

upper connector rod is $$k_{r1} \left( = \frac{E_r A}{l_{r1}} \right),$$

lower connector rod is $$k_{r2} \left( = \frac{E_r A}{l_{r2}} \right),$$

and composite specimen $$k_s \left( = \frac{E_s A}{l_s} \right),$$

is where E and l are the modulus and length of each component. Subscripts r and s represent upper and lower connector rods and composite specimen, respectively; subscripts 1 and 2 refer to upper connector rod and lower connector rod, respectively. In order for measurements of cantilever beam deflection to reflect specimen deformation due to shrinkage, without contributions from rod deformation, the ratio of $k_r$ to $k_b$ should be relatively large (i.e., >100, assuming $l_{r1}=l_{r2}$) so that the deformation of upper and lower connector rods become negligible.

Prior to the use of tensometer 100, an operator should calibrate voltage to displacement of tensometer 100. A constant known weight (e.g., a fishing sinker) may be used as a load source (P) to characterize the force exerted on cantilever beam 102. For each hanging location along cantilever beam 102 from clamped proximal end 102a (x), voltage reading ($\Delta V$) of LVDT 112 is recorded and a factorized beam displacement ($\delta_c = \delta \cdot E \cdot I$) is calculated from the following equation:

$$\delta_c = \frac{Px^2(3l-x)}{6} \quad (3)$$

Figure 6:
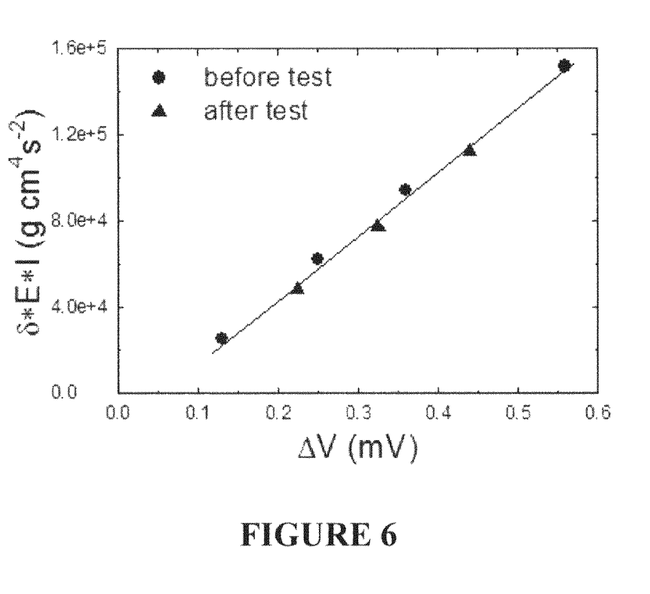
FIG. 6 illustrates an exemplary calibration curve for a tensometer in accordance with an embodiment of the present invention.

In equation (3), the ratio of x to h is greater than or equal to eight (i.e., $x/h \geq 8$). FIG. 6 displays an exemplary $\delta_c$ versus $\Delta V$ calibration curve, which was generated by varying the sinker location along cantilever beam 102. In a PS measurement, the force (F), as used in equation (2), corresponding to a sample position can be calculated through the following equation:

$$F = \frac{6S\Delta V}{a^2(3l-a)} \quad (4)$$

where S is the slope of the $\delta_c$–$\Delta V$ relationship as shown in FIG. 6.

Embodiments of tensometer 100 can be used to characterize the kinetics of polymerization shrinkage and elastic modulus development for restorative materials. These are exemplary metrics that can be used in the modeling and simulation of stresses incurred during the polymerization of dental restoratives under clinically relevant configurations, as well as in the development of new materials. For example, development of polymerization shrinkage (or polymerization kinetics) is an important parameter for processing and developing polymer-based products. In addition, elastic modulus development during network reaction is a key measure of polymerization completion level and the materials' ability to transfer stress to their surrounding constraints. One method involves conducting two independent polymer stress measurements of samples, having same size but at different locations on the cantilever beam using a tensometer in accordance with an embodiment of the present invention. The resulting two sets of polymerization stress data obtained are used to deduce the shrinkage and modulus development. Samples having identical sizes will have the same amount of shrinkage at any given time after polymerization is initiated. These types of measurements can also be applied to measure thermal and swelling expansion of polymeric and non-polymeric materials.

Figure 7:
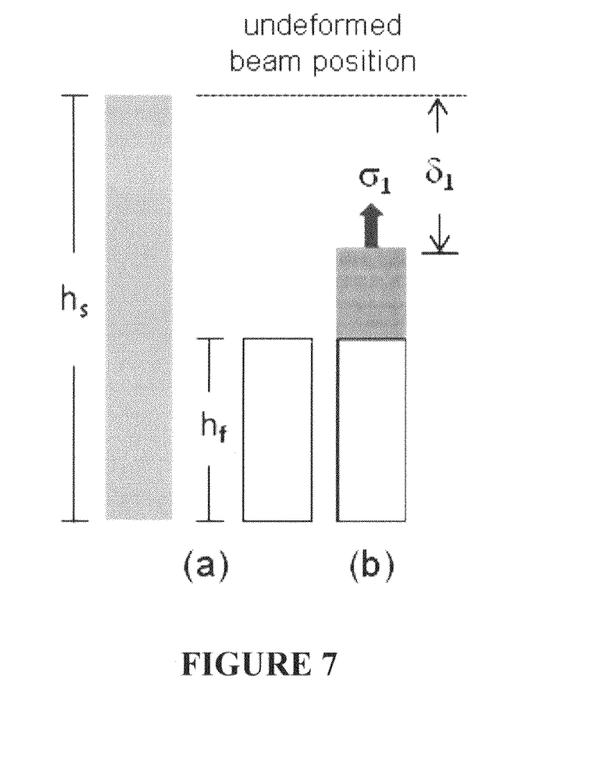
FIG. 7 provides an exemplary pictorial illustration of the development of polymerization stress during curing of a composite specimen used in accordance with an embodiment of the present invention.

At any instantaneous time t, the development of polymerization stress can be decomposed into two competing processes. FIG. 7 provides a pictorial illustration of the development of polymerization stress as two competing processes. First, a specimen shrinks freely to height $h_f$ from its original height $h_o$ (FIG. 7(a)). Second, the freely shrunken specimen is pulled back by the beam to an equilibrium position, and the cantilever beam is deflected to position $\delta_t$ (FIG. 7(b)). These two processes occur simultaneously, and the entire development of polymerization can be a series of simultaneous shrink-pull actions, until the final state is obtained.

Figure 8:
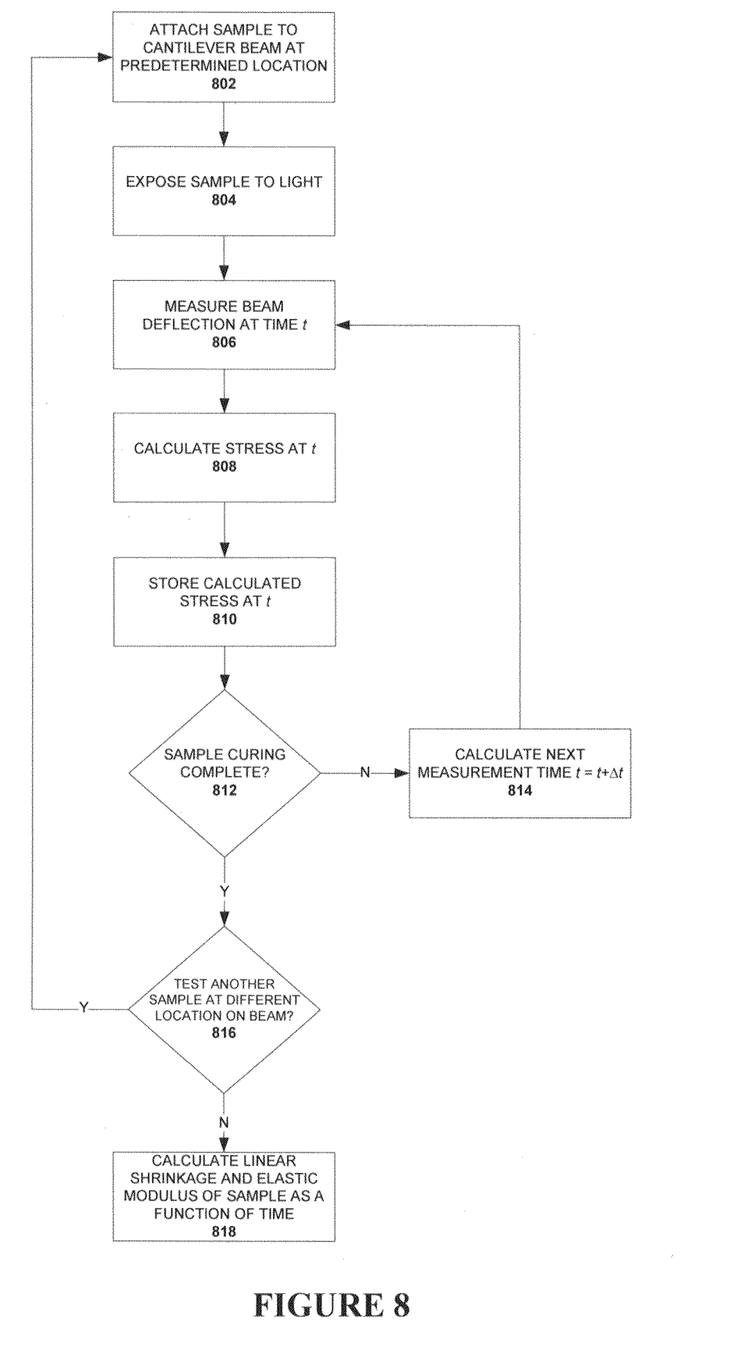
FIG. 8 is a flow chart showing a method of determining the development of polymeric stress in accordance with an embodiment of the present invention.

FIG. 8 illustrates a method of measuring polymerization shrinkage (or polymerization kinetics) and elastic modulus development using tensometer 100. At step 802, composite specimen 124 is coupled to cantilever beam 102 at a predetermined position on cantilever beam 102 using upper connecting rod 114. At step 804, composite specimen 124 is exposed to curing light from light source 126. At step 806, LVDT 112 measures deflection of cantilever beam 102 due to shrinkage of composite specimen 124 at a predetermined time t. At each time interval, composite specimen 124 exerts a shrink force while cantilever beam 102 exerts a pull force. In each shrink-pull action, a stress is applied from cantilever beam 102 to the freely shrunk composite specimen 124, resulting in a deformation (elongation) of composite specimen 124. At step 808, processor 126 calculates the instantaneous stress ($\sigma$) at time t applied from cantilever beam 102 to the freely shrunk composite specimen 124 using the beam deflection ($\delta$) measurement at time t obtained by LVDT 112 at step 806. At step 810, processor 126 stores instantaneous stress ($\sigma(t)$) and deflection ($\delta(t)$) calculated at time t.

At decision step 812, processor 126 determines whether composite specimen 124 curing is complete. If, at decision step 812, processor 126 determines that composite specimen 124 curing is incomplete, then at step 814, processor 126 increases the measurement time by a predetermined interval t. At step 803, LVDT 112 measures deflection of cantilever beam 102 due to shrinkage of composite specimen 124 at the next predetermined time t. If, at decision step 812, processor 126 determines that composite specimen 124 curing is complete, then at decision step 816, processor 126 determines whether to test an additional sample of same composite specimen 124. If at decision step 816, processor 126 determines to test an additional sample of same composite specimen 124, then at step 802, another sample of same composite specimen 124 having same height $h_o$ as previous sample is coupled to cantilever beam 102 at a second predetermined position on cantilever beam 102 using upper connecting rod 114. The magnitude of instantaneous stress ($\sigma_t$) depends on time t and sample location, and can be related to the corresponding deformation (as shown in FIG. 7(b), shaded portion) as:

$$\sigma(t) = E(t)\varepsilon(t) = E\frac{[h_o - h_t(t) - \delta(t)]}{h_t(t)} \quad (5)$$

where $\delta$ is the cantilever beam deflection at time t, and $\varepsilon(t)$ is the strain corresponding to $\sigma(t)$ and E(t) is the elastic modulus of composite specimen 124 at time t, respectively.

If, at decision step 816, processor 126 determines not to test an additional sample of same composite specimen 124, then at step 818, using instantaneous stress stored at step 810 for each t and for each sample, processor 126 determines linear shrinkage S and elastic modulus E of composite specimen 124 at each instant of time t using equations (6)-(8).

$$h_f = \frac{h_o(\lambda-1) + \delta_1 - \lambda\delta_2}{\lambda-1} \quad (6)$$

$$S = 1 - \frac{h_f}{h_o} \quad (7)$$

-continued $$E = \frac{\sigma_t h_o(\lambda - 1)}{\lambda(\delta_2 - \delta_1)} \quad (8)$$

where $\lambda = \sigma_1/\sigma_2$; $\sigma_1$ and $\sigma_2$ are the stress ($\sigma$); $\delta_1$ and $\delta_2$ are the beam deflection ($\delta$), obtained for the composite specimens at first and second predetermined positions on cantilever beam at each instant of time t.

A more complete understanding of the present invention can be obtained by referring to the following illustrative examples of the practice of the invention, which examples are not intended, however, to be unduly limitative of the invention.

EXAMPLE

Evaluation of the development of polymer stresses in TPH Micro Matrix Restorative: lot #070403, shade A1, Dentsply-Caulk.

In this investigation, a commercial composite (TPH Micro Matrix Restorative: lot #70403, shade A1, Dentsply-Caulk, Milford. Del., USA) was used as a test material to demonstrate the validity of our newly designed tensometer in the evaluation of PS. TPH is based on a visible-light activated, urethane-modified Bis-GMA and TEGDMA (1:1 mass ratio) filled primarily with a barium boron aluminum silicate glass at 78% mass fraction (filler volume fraction is approx. 57%). The specimen/rod diameter was 6.0 mm. The visible-light curing pen light (Spectrum Curing Unit, Denstply-Caulk, Milford, Del.) was attached to the lower quartz rod with an opaque flexible light guide. The faces of quartz rods connected to the specimen were silanized to promote adhesion between the composite sample and rods. The silanization process was conducted by applying a 1% by mass acetone solution of 3-methacryloxypropyltrimethoxysilane (MPTMS; Gelest, Morrisville, Pa.) activated with 0.1% by mass formic acid. The rods were then heated at 60° C. for 12 h. Specimen height was determined using a rigid spacer of known height inserted between the two rods. A flexible tygon tubing sleeve with an injection hole and a smaller air-release hole was used to encase the rods and composite specimens. The composite pastes were delivered to this sample chamber by means of a syringe fitted with a tapered tube through the larger hole in the sleeve. The composite pastes were irradiated for 60 s through the lower quartz rod to initiate photo-polymerization, and the development of PS was monitored for 60 min. The light intensity, measured by a Demetron Model 100 radiometer (Demetron Research, Danbury, Conn.) was (510±25) mW/cm$^2$ at the upper end of the top quartz rod where the sample was bonded. We note that the polymerization stress from chemical-cure can be measured in the same tensometer.

During irradiation, chemical bonds establish between the polymeric composite and silanized quartz rod-end surfaces via a bridging of polymer macrogel networks, thus permitting transmission of dimensional change into a measured stress. Both polymerization shrinkage and heat can contribute to the dimensional change. However, the contribution from latter is of minor importance or negligible, especially in highly filled composites such as the one used in the current study.

Figure 9:
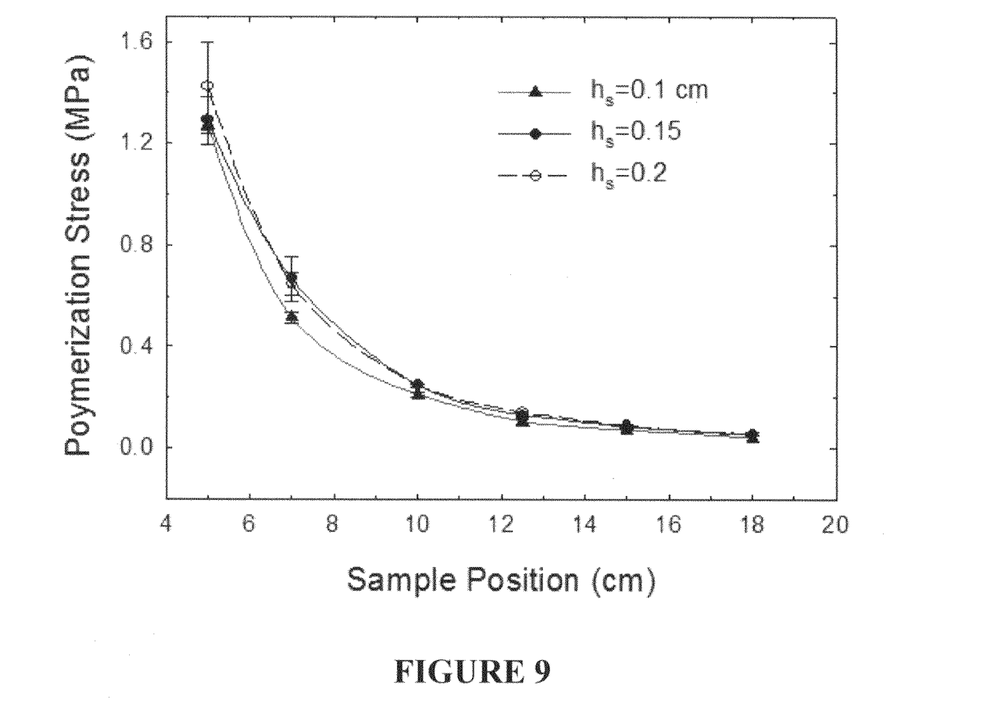
FIG. 9 is an exemplary plot showing the development of polymerization stresses measured using an apparatus in accordance with an embodiment of the present invention.

Based on our analyses, a new tensometer equipped with an aluminum beam (l=24.5 cm, h=1.0 cm. and w=0.625 cm) was constructed. FIG. 9 displays PS values determined as a function of effective beam length (sample positions) for different sample heights (data values are provided in Table 1).

TABLE 1

| Sample Position (effective beam length) | Sample Height (cm) | | | | | |
|---|---|---|---|---|---|---|
| | 0.1 | | 0.15 | | 0.2 | |
| cm | PS | SD | PS | SD | PS | SD |
| 5 | 0.7388 | 0.0175 | 0.7504 | 0.0561 | 0.8280 | 0.0995 |
| 7 | 0.2986 | 0.0121 | 0.3878 | 0.0521 | 0.3762 | 0.0262 |
| 10 | 0.1222 | 5.8173e−3 | 0.1435 | 3.3586e−3 | 0.1435 | 3.3586e−3 |
| 12.5 | 0.0601 | 6.7173e−3 | 0.0756 | 5.8173e−3 | 0.0814 | 0.0000 |
| 15 | 0.0407 | 0.0000 | 0.0485 | 3.3586e−3 | 0.0504 | 3.3586e−3 |
| 18 | 0.0233 | 0.0000 | 0.0291 | 0.0000 | 0.0310 | 3.3586e−3 |

Figure 10:
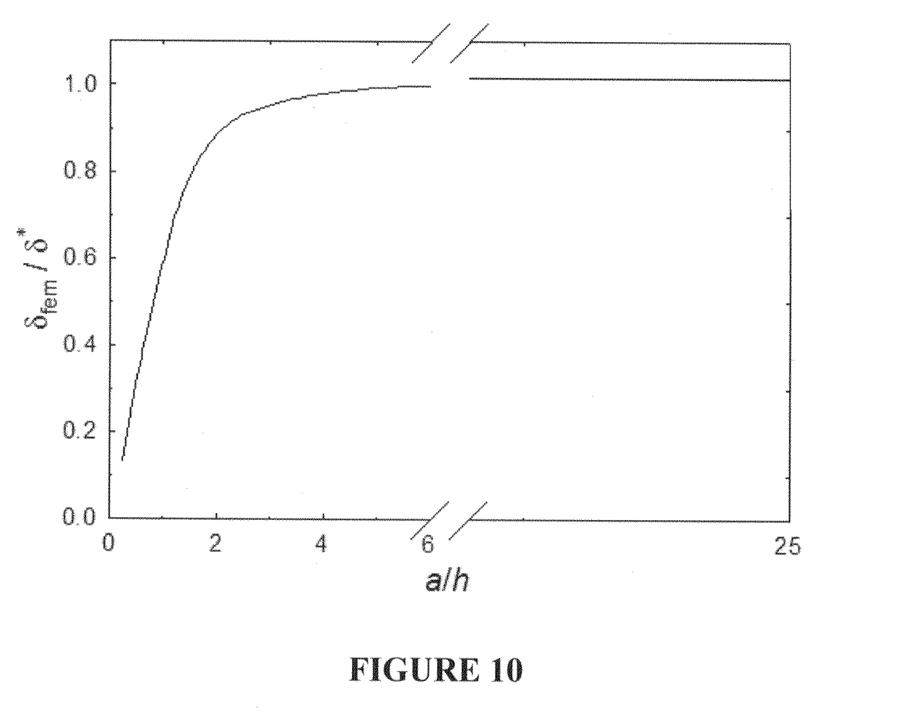
FIG. 10 is an exemplary plot comparing analytical solution versus the finite element solution on deflection at the tip of a cantilever beam used in accordance with an embodiment of the present invention.

PS increased with a decrease in the effective beam length since the rigidity of tensometer system increased. Additionally, PS increased as a cubic polynomial function of decreasing sample location. This is because the system's rigidity (beam spring constant) is a cubic function of beam length (see equation (1)). This functional agreement between the experimental results and theoretical calculation demonstrates the sensitivity of system to the presence of sample deformation and the accuracy of measurement. In contrast, a nearly linear relationship between PS and sample location (effective beam length) was found when the earlier cantilever-beam based tensometer was used. The previous tensometer had a beam height of 4.0 cm; six different effective beam lengths (5.0 cm, 7.0 cm, 10.0 cm, 12.5 cm, 15.0 cm, and 18.0 cm) were used to match the different compliances related to dental restoration configurations. Under this range of aspect ratios (a/h=1.25 to 4.5), the shear deformation contributes significantly to the beam deflection; thus, the applicability of equation (1) is violated. In such case, equation (1) would need to be modified as follows:

$$\delta^* = F\left(\frac{a^2(3l-a)}{6EI} + \frac{h^2 l(1+v)}{4EI}\right) \quad (9)$$

where v is the Poisson's ratio of the beam material. In the derivation of equation 5, a cantilever beam with a narrow rectangular cross section was considered having length "a" and bent by a force "F" applied at the beam end of "a"; the displacement solution at the beam end can be obtained analytically based on the theory of elasticity. For the subject tensometer system, the beam displacement corresponding to the LVDT location, δ, is determined by the superposition of the displacement at "a" due to the stresses and strains as well as the displacement due to a rigid body rotation of the beam cross section at "a." The first term on the right hand side of equation (9) represents the bending contribution, while the second term represents shearing and diminishes as the ratio of a/h increase. A near linear relationship between PS and beam length obtained by the earlier cantilever-beam based tensometer is attributed to the dominance of shearing, where the shearing has a linear relationship with the beam aspect ratio. A finite element analysis was invoked to obtain the displacement-aspect ratio relationship of the cantilever beam depicted in FIG. 4. FIG. 10 shows good agreement between the solution of equation (9) and our finite element analysis for a wide range of aspect ratios, except when the sample location is comparable to beam height (i.e., a/h≤2). This indicates that equation (9) can be used for any beam length (i.e., any combined situation of bending and shearing) to properly calculate the PS. The discrepancy between the analytical and finite element solutions shown in FIG. 10 is due to the edge effect. Practically, the sample location would not be that close to the beam edge.

It is thought that the system and method of the present invention and many of its attendant advantages will be understood from the foregoing description and it will be apparent that various changes may be made in the form, construction arrangement of parts thereof without departing from the spirit and scope of the invention or sacrificing all of its material advantages, the form hereinbefore described being merely a preferred or exemplary embodiment thereof.

I claim:

1. A method for determining the development of polymeric shrinkage during polymer material curing, the method comprising:
    curing a first sample of the polymeric material having a predetermined length, wherein the first sample of the polymeric material is coupled to a cantilever beam at first predetermined position;
    measuring deflection of the cantilever beat at predetermined time intervals until the polymeric material curing is complete;
    coupling a second sample of the polymeric material having the predetermined length to the cantilever beam at a second predetermined position;
    curing the second sample of the polymeric material;
    measuring deflection of the cantilever beam at the predetermined time intervals until the second sample of the polymeric material curing is complete; and
    determining linear shrinkage and elastic modulus of the polymeric material at the predetermined time intervals.

2. The method of claim 1, further comprising:
    calculating shrinkage stress of the polymeric material exposed to curing light at each of the predetermined time intervals; and
    storing the stress values at each of the predetermined time intervals.

3. The method of claim 2, wherein the curing light source is ultraviolet light.

4. The method of claim 1, wherein the curing the first and second samples of the polymeric material comprises exposing the polymeric material to a light source.

5. The method of claim 1, wherein the curing the first and second samples of the polymeric material enables shrinkage of the polymeric material.

6. The method of claim 5, wherein the measuring deflection of the cantilever beam at the predetermined time intervals comprises detecting the shrinkage of the polymeric material.

* * * * *